United States Patent
Fadler et al.

(10) Patent No.: US 7,093,976 B2
(45) Date of Patent: Aug. 22, 2006

(54) MOTOR-ADJUSTABLE X-RAY SYSTEM

(75) Inventors: Franz Fadler, Hetzles (DE); Udo Heinze, Erlangen (DE); Martin Vierbücher, Ebern (DE)

(73) Assignee: Siemens Aktiengesellschaft, Munich (DE)

( * ) Notice: Subject to any disclaimer, the term of this patent is extended or adjusted under 35 U.S.C. 154(b) by 149 days.

(21) Appl. No.: 10/964,071

(22) Filed: Oct. 12, 2004

(65) Prior Publication Data

US 2005/0105692 A1    May 19, 2005

(30) Foreign Application Priority Data

Oct. 14, 2003   (DE) ................... 103 47 735

(51) Int. Cl.
*H05G 1/02*    (2006.01)
(52) U.S. Cl. ..................... 378/197; 378/117
(58) Field of Classification Search ........ 378/193–198, 378/114, 115, 117
See application file for complete search history.

(56) References Cited

U.S. PATENT DOCUMENTS 5,848,126 A * 12/1998 Fujita et al. ............... 378/195
5,930,328 A * 7/1999 Nakamura et al. ........... 378/91
6,409,381 B1   6/2002 Siebenhaar et al. ......... 378/197

FOREIGN PATENT DOCUMENTS

DE         42 37 013 A1    5/1994
DE         197 15 642 C2   5/2001

\* cited by examiner

*Primary Examiner*—Edward J. Glick
*Assistant Examiner*—Jurie Yun
(74) *Attorney, Agent, or Firm*—Brinks Hofer Gilson & Lione

(57) ABSTRACT

An X-ray system, comprises a motor-adjustable C-arm, an input device which has a first actuating device and is mechanically connected to the C-arm, a dead man's switch, which is mechanically connected to the C-arm, and a pattern recognition module which cooperates with the input device and the dead man's switch, and is provided to determine a classification of actuating signal patterns generated via the first actuating device. A first signal group is activatable when the dead man's switch is actuated, and a second signal group is activatable when the dead man's switch is not actuated.

21 Claims, 2 Drawing Sheets

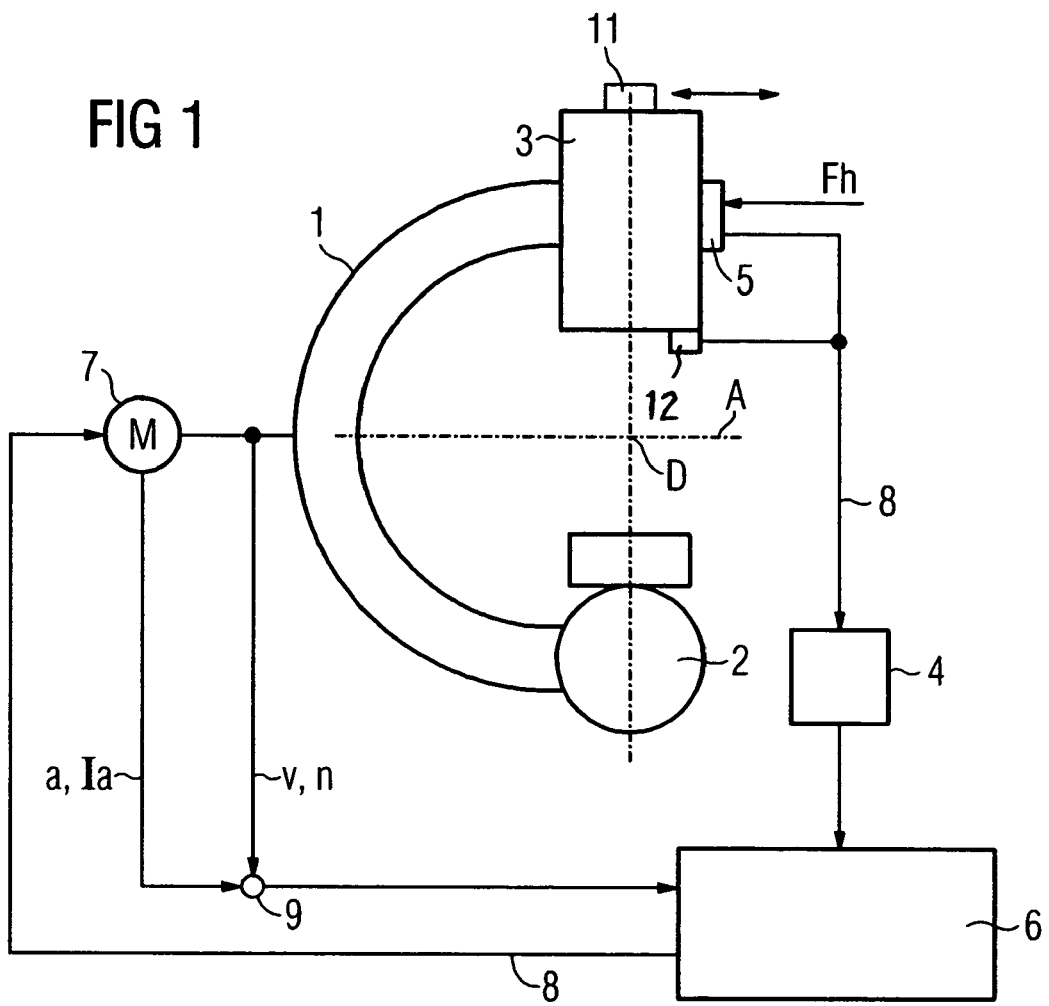
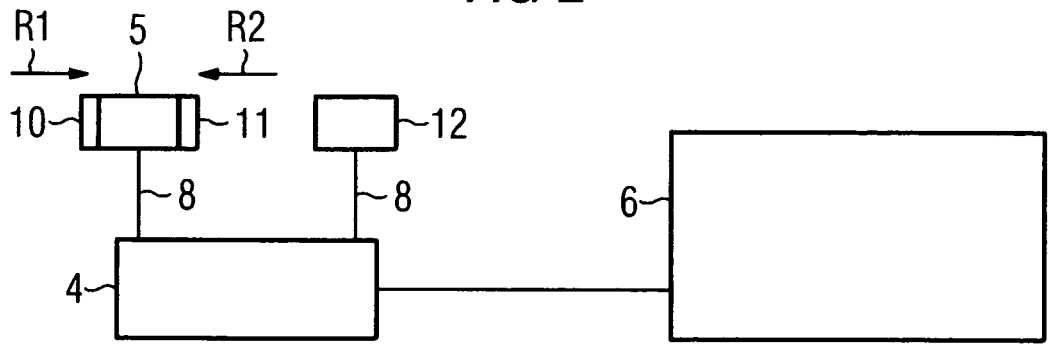

MOTOR-ADJUSTABLE X-RAY SYSTEM

FIELD OF THE INVENTION

The invention relates to X-ray systems, and more particularly, to an X-ray system with a motor-adjustable C-arm.

BACKGROUND OF THE INVENTION

A C-arm X-ray system is known for instance from German Patent Disclosure DE 42 37 013 A1. The X-ray system known from DE 42 37 013 A1 has a handle on a picture-taking system supported on the C-arm, and a force pickup is associated with this handle. A user control force which can be detected serves as a guide variable in a closed-loop control circuit, and an acceleration of the motor-adjustable C-arm is the controlled by the variable. In this way, the user is meant to be given the impression that he is moving the X-ray system with substantially smaller masses or lesser moments of inertia. For tripping further control functions, which go beyond purely controlling motion, buttons or keys are pressed by the user. Such buttons are typically disposed not on the C-arm or on the picture-taking system connected to the C-arm but rather on a separate control unit. This arrangement may make operating the X-ray system ergonomically unfavorable and time-consuming.

OBJECT AND SUMMARY

The present invention is defined by the appended claims. This description summarizes some aspects of the present embodiments and should not be used to limit the claims.

An X-ray system with a motor-adjustable C-arm may make time-saving, ergonomically favorable operations possible. The X-ray system includes a motor-adjustable C-arm, and on the C-arm, or on a part mechanically connected to the C-arm, such as a picture-taking system, both an input device, which may have at least one actuating device, and a dead man's switch are disposed. Preferably, the actuating device is designed on the order of a handle or a so-called servo railing disposed on the C-arm; the dead man's switch is also disposed on this railing or in its vicinity, and its actuation is a prerequisite for adjusting the C-arm via the input device. Both the input device that has the actuating device and the dead man's switch cooperate with a pattern recognition module, which is preferably integrated with a closed-loop control unit of the X-ray system. The pattern recognition module makes it possible to classify actuating signal patterns, generated via the actuating device, in two signal groups. A first signal group may include actuating signal patterns which are activatable when the dead man's switch is actuated, or in other words which are operative for operating the X-ray system. The second signal group, conversely, may include actuating signal patterns that can be generated via the actuating device and that are activatable when the dead man's switch is not actuated. This arrangement does not necessarily preclude the possibility that actuating signal patterns assigned to the second signal group are also activatable, or in other words enabled, when the dead man's switch is actuated. Preferably, however, the actuating signal patterns of the first signal group are usable solely when the dead man's switch is actuated, and the actuating signal patterns of the second signal group are usable solely when the dead man's switch is not actuated.

In one advantageous feature, adjusting the C-arm of the X-ray system would be possible only if, in addition to an actuating device, for instance in the form of a handle or a railing, a dead man's switch is also pressed. As such, unintended movements of the C-arm may be practically precluded. For other functions that are not safety-critical, conversely, it is possible to dispense with the actuation of a dead man's switch.

For tripping such other functions, separate switches or buttons may be provided. If these switches or buttons are disposed separately from the C-arm, for instance on a separate control unit, this arrangement would be a hindrance to easy operation of the X-ray system. On the other hand, the possibilities for providing additional switches or buttons on the C-arm itself are also limited. This may be evident particularly in cases in which a user control handle or actuating device, intended for adjusting the C-arm, is embodied as a servo railing, which is large in size in comparison to radiological equipment carried on the C-arm. Thus, because of the additional switches and buttons, the ergonomic advantages of a large-sized user control handle could be utilized only with considerable restrictions. These restrictions are rescinded according to this feature, because the actuating device intended for adjusting the C-arm can additionally be used for still other functions of the X-ray system that are not safety-critical. In this last case, in contrast to the motion control of the C-arm, no actuation or availability of the dead man's switch is contemplated.

The classification of an actuating signal pattern, generated with the actuating device disposed preferably on the C-arm, into one of the signal groups preferably depends not only whether the dead man's switch is actuated but also on the time structure of the actuating signal pattern. Particularly in the case of a large-sized actuating device disposed on the C-arm, precautions may be taken to prevent unintended tripping of control functions. With respect to actuating signal patterns of the second signal group, such a precaution is preferably taken such that the pattern recognition module, as part of the control of the X-ray system, accepts only brief actuations of the actuating device as belonging to the second signal group. Preferably, the duration of a time slot for an actuating signal pattern of the second signal group, for instance tapping the actuating device once or twice, is at most 1 second, for example. A likelihood of an incorrect operation is reduced sufficiently by such predetermination of the time structure of the actuating signal pattern for functions that are assigned to the second signal group and that in comparison to the functions assigned to the first signal group, and in particular shifting of the C-arm, are not as critical to safety.

In another advantageous feature, the input device has a second actuating device, for instance of force and/or travel pickup, which is actuatable preferably together with the first actuating device via a single operating or control handle, in particular a hoop or a railing on the C-arm. In a desirable way, the input device may be embodied so as to detect directional components of the force, exerted by the user, in all directions in space. If the input device is used in accordance with the first signal group, that is, with the dead man's switch actuated, to control the motion of the C-arm, then a direct specification of a direction is possible for adjusting the C-arm via a single actuation handle. The same actuation handle, cooperating with two actuating devices, in particular force pickups, or in some other way generating information about the actuation direction, is preferably simultaneously provided for also picking up actuating signal patterns that belong to the second signal group and that include a chronologically correlated actuation of the operating handle in different and in particular opposite directions, or an actuation correlated chronologically in some other way of a plurality of actuating devices. This kind of chronologically correlated actuation including a plurality of actuation directions is made for instance via a back and forth motion, or in other words shaking an operating handle and in particular a railing a single time.

A still another advantageous feature is that in an X-ray system, an input device that is present for adjusting a C-arm and that includes sensor elements, such as force or travel pickups, may be simultaneously used to perform still other functions in addition to the motion control. The controller of the X-ray system in this respect may evaluate the time structure of an actuation signal in the manner of recognizing a gesture. There is no need for the user to change to an operator control menu to call up special functions.

Illustrative and exemplary embodiments of the invention are described in further detail below with reference to and in conjunction with the figures.

BRIEF DESCRIPTION OF THE DRAWINGS

FIG. 1 schematically shows an X-ray system with a motor-adjustable C-arm;

FIG. 2 is a block diagram showing parts of a controller of the X-ray system of FIG. 1.

DETAILED DESCRIPTION OF DRAWINGS

Figure 3A:
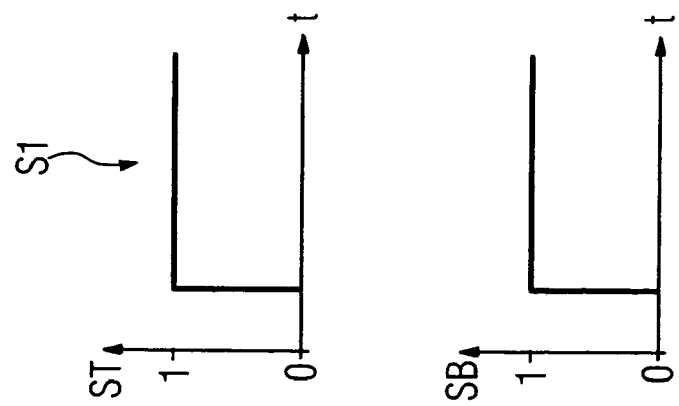
FIGS. 3a, 3b, and 3c show graphically alternate examples of an actuating signal pattern.

Parts and parameters corresponding to one another are identified by the same reference numerals in both drawings.

An X-ray system, shown schematically in FIG. 1, includes an angularly and orbitally adjustable C-arm 1, which on one end has an X-ray source or emitter 2 and on the other has a picture-taking system 3. A pivot point pertaining to the orbital adjustment is marked D, and an axis pertaining to the angular adjustment is marked A. An input device 5 includes force and/or travel pickups, is disposed on the picture-taking system 3 and is intended for picking up or sensing a manual force Fh of the user. The input device 5 preferably has as its operating handle at least one railing, which is disposed on the C-arm 1 and/or on the items of X-ray equipment 2, 3 and which furnishes precise directional information about the manual force Fh. Information pertaining to the amount and direction of the force Fh is carried via a line 8 and a pattern recognition module 4 to a closed-loop control unit 6. This closed-loop control unit 6 also communicates via lines 8 with an electric motor 7, which serves to adjust the C-arm 1. Information about an acceleration a of the X-ray system 1, 2, 3, an armature current 1a of the electric motor 7, a speed v of the X-ray system 1, 2, 3, and an rpm n of the electric motor 7 are carried to the closed-loop control unit 6 via a comparator 9. For moving the C-arm 1 in the orbital and/or angular direction arbitrarily, a dead man's switch 12 is or must be actuated in addition to the input device 5; this dead man's switch 12 is likewise disposed on the picture-taking system 3, spaced slightly apart from the input device 5.

A cooperation of the input device 5 and the dead man's switch 12 with the pattern recognition module 4 will now be described in further detail in conjunction with FIG. 2. The input device 5, preferably embodied as a servo railing, may include a first actuating device 10 and a second actuating device 11, which are intended for picking up user control forces Fh in a first actuation direction R1 and a second actuation direction R2, respectively. Furthermore, the input device 5 is equipped with sensor elements (not shown), which may furnish substantially complete directional information about the user control force Fh. The direction of the user control force Fh may correspond to the direction in which the C-arm 1 is to be adjusted.

Various modes of operation of the input device 5 and dead man's switch 12 will now be explained in conjunction with FIGS. 3a through 3c. In each of these figures, as a function of time t, a course of a dead man's signal ST, which can be tripped with the dead man's switch 12, and a course of an actuation signal SB, which can be tripped with the input device 5, are plotted. Taking FIG. 3a as an example, both the input device 5 and the dead man's switch 12 are actuated simultaneously and for a relatively long duration. The actuating signal pattern generated by means of the input device 5 is assigned to a first signal group S1, which is assigned to the motion controller of the C-arm 1. Unintended movement of the C-arm 1 is practically precluded, since an assignment to the first signal group occurs only when the dead man's switch 12 is actuated.

Figure 3B:
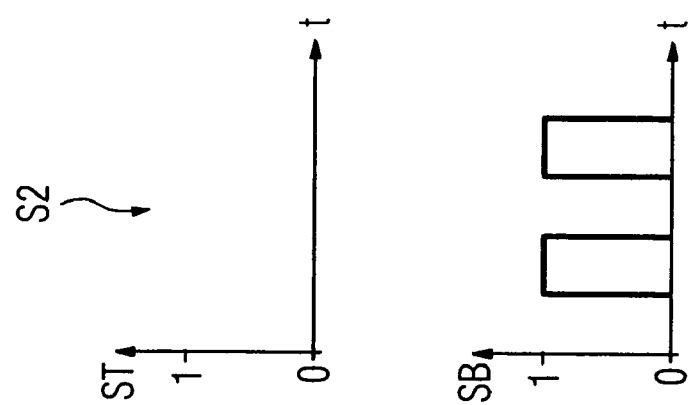

In the example of FIG. 3b, the dead man's switch 12 is not actuated, while the input device 5 is actuated with two pulses, whose total duration is less than 1 second or other duration. This actuating signal pattern is assigned to a second signal group S2, which includes control functions that go beyond adjusting the C-arm 1. For instance, by tapping the input device 5 twice, on the order of a double click, the function of axial fidelity of the adjustment of the C-arm 1 is selected. In this function, the C-arm 1 can be adjusted only exactly in the angular direction, or only exactly in the orbital direction. By tapping the input device 5 once, corresponding to one of the pulses shown in FIG. 3b, the position of the C-arm 1 at that time can preferably be marked. Thus, in a simple way, a latching point ("soft notch") of the C-arm can be defined which can later be approached in a simplified way. Further additional control functions can for instance be tripped by actuating the actuating devices 10, 11 in rapid succession, in particular within less than 1 second, for instance by moving an operating handle, which cooperates mechanically with both actuating devices 10, 11, in both actuation directions R1, R2, or at least loading it with a user control force Fh. The common feature of the above-described actuating signal patterns of the second signal group S2 is that the dead man's switch 12 is not actuated. The assignment of each actuation signal to one of the signal groups S1, S2 is done via the pattern recognition module 4, which is for instance integrated with the closed-loop control unit 6. Inputting an actuation signal from the second signal group S2 while the dead man's switch 12 is actuated is preferably generally precluded. As a result, on the one hand, a desirably simple input of actuating signal patterns that belong to the second signal group may be possible. On the other hand, unintentional tripping of a motion of the C-arm 1 while choosing a special function assigned to the second signal group S2 may be precluded.

Figure 3C:
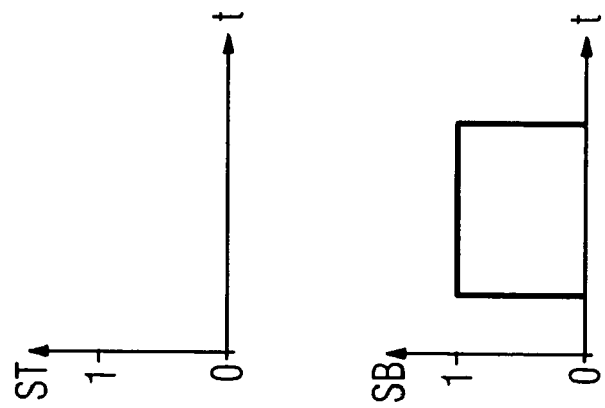

In the example of FIG. 3c, only the input device 5 is actuated, but is actuated over a period of time that is longer than the short-time signal assigned to the second signal group S2. Simultaneously, the dead man's switch 12 remains unactuated. In this case, an unintended actuation of the input device 5 is assumed. Thus, the actuating signal pattern of FIG. 3c trips neither a motion of the C-arm 1 nor any other control function.

The invention claimed is:
1. An X-ray system, comprising:
a motor-adjustable C-arm;

an input device having a first actuating device and mechanically connected to the C-arm;

a dead man's switch mechanically connected to the C-arm; and a pattern recognition module cooperating with the input device and the dead man's switch, the pattern recognition module operable to determine a classification of actuating signal patterns generated by the first actuating device, wherein a first signal group is activatable when the dead man's switch is actuated, and a second signal group is activatable when the dead man's switch is not actuated.

2. The X-ray system of claim 1, wherein a first actuating signal pattern of the first signal group is assigned to a motion controller of the C-arm.

3. The X-ray system of claim 1, wherein a first actuating signal pattern generated by a brief actuation of the first actuating device is assigned to the second signal group.

4. The X-ray system of claim 2, wherein a second actuating signal pattern of the second signal group is generated by brief actuation of the first actuating device.

5. The X-ray system of claim 3, wherein a time duration of the first actuating signal pattern of the second signal group is less than about one second.

6. The X-ray system of claim 1, wherein a first actuating signal pattern generated by actuating the first actuating device twice is assigned to the second signal group.

7. The X-ray system of claim 2, wherein a second actuating signal pattern generated by actuating the first actuating device twice is assigned to the second signal group.

8. The X-ray system of claim 3, wherein a second actuating signal pattern generated by actuating the first actuating device twice is assigned to the second signal group.

9. The X-ray system of claim 4, wherein the second actuating signal pattern generated by actuating the first actuating device twice is assigned to the second signal group.

10. The X-ray system of claim 1, wherein the input device further comprises a second actuating device.

11. The X-ray system of claim 2, wherein the input device further comprises a second actuating device.

12. The X-ray system of claim 3, wherein the input device further comprises a second actuating device.

13. The X-ray system of claim 6, wherein the input device further comprises a second actuating device.

14. The X-ray system of claim 7, wherein the input device further comprises a second actuating device.

15. The X-ray system of claim 10, wherein an actuating signal pattern, generated via a chronologically coherent actuation of the first and second actuating devices, belongs to the second signal group.

16. The X-ray system of claim 11, wherein a second actuating signal pattern, generated via a chronologically coherent actuation of the first and second actuating devices, belongs to the second signal group.

17. The X-ray system of claim 12, wherein the first actuating signal pattern, generated via a chronologically coherent actuation of the first and second actuating devices, belongs to the second signal group.

18. The X-ray system of claim 13, wherein the first actuating signal pattern, generated via a chronologically coherent actuation of the first and second actuating devices, belongs to the second signal group.

19. The X-ray system of claim 14, wherein the second actuating signal pattern, generated via a chronologically coherent actuation of the first and second actuating devices, belongs to the second signal group.

20. The X-ray system of claim 10, wherein actuation directions of the first and second actuating devices are oriented opposite to one another.

21. The X-ray system of claim 15, wherein actuation directions of the first and second actuating devices are oriented opposite to one another.

* * * * *